United States Patent [19]

Morrissey et al.

[11] Patent Number: 5,504,064
[45] Date of Patent: Apr. 2, 1996

[54] TREATMENT OF BLEEDING WITH MODIFIED TISSUE FACTOR IN COMBINATION WITH AN ACTIVATOR OF FVII

[75] Inventors: James H. Morrissey; Philip C. Comp, both of Oklahoma City, Okla.

[73] Assignee: Oklahoma Medical Research Foundation, Oklahoma City, Okla.

[21] Appl. No.: 21,615

[22] Filed: Feb. 19, 1993

Related U.S. Application Data

[63] Continuation-in-part of Ser. No. 882,202, May 13, 1992, Pat. No. 5,374,617, and Ser. No. 683,682, Apr. 10, 1991.

[51] Int. Cl.[6] .......................... A61K 35/14; A61K 38/48; A61K 38/16; C07K 14/745
[52] U.S. Cl. .............................. 514/8; 530/384; 530/350; 530/395; 514/12; 514/21
[58] Field of Search ................................. 514/8, 802, 12, 514/21, 834; 530/384, 350, 830, 380, 381, 829, 395

[56] References Cited

U.S. PATENT DOCUMENTS

| | | | |
|---|---|---|---|
| 4,456,591 | 6/1984 | Thomas | 514/8 |
| 5,180,583 | 1/1993 | Hedner | 514/2 |
| 5,298,599 | 3/1994 | Rezaie et al. | 530/350 |
| 5,346,991 | 9/1994 | Roy et al. | 530/350 |

FOREIGN PATENT DOCUMENTS

| | | |
|---|---|---|
| 0225160 | 6/1987 | European Pat. Off. . |
| 0278776 | 3/1988 | European Pat. Off. . |
| 8807543 | 10/1988 | WIPO . |
| 8809817 | 12/1988 | WIPO . |

OTHER PUBLICATIONS

Hapak, et al., "The location of the active site of Factor VIIa above the membrane surface is altered by either full-length or truncated tissue factor," *FASEB Journal* 6:A330, Abstract No. 1900 (1992).

De Sousa, et al., "Factor VII hyperactivity in acute myocardial thrombosis, a relation to the coagulation activation," *Thrombosis Research*, 51:165–173 (1988).

Poggio, et al., "Factor VII clotting assay: influence of different thromboplastins and Factor VII-deficient plasmas," *Thrombosis and Haemostasis*, 65:160–164 (1991).

Paborsky, et al., "Purification of recombinant human tissue factor," *Biochemistry*, 28:8072–8077 (1989).

Paborsky and Harris, "Post-translational modifications of recombinant human tissue factor," *Thrombosis Research*, 60:367–376 (1990).

Hoffman, et al., "Factor VII activity state in coronary artery disease," *J. Lab. Clin. Med.*, 111:475–481 (1988).

Gordon, et al., "Augmented Hageman factor and prolactin titers, enhanced cold activation of factor VII, and spontaneous shortening of prothrombin time in survivors of myocardial infarction," *J. Lab. Clin. Med.*, 109:409–413 (1987).

Mitropoulos, "Hypercoagulability and Factor VII in hypertriglyceridemia," *Seminars in Thrombosis and Hemostasis*, 14:246–251 (1988).

Scarabin, et al., "Is Factor VII activation in pregnant women relevant to fetal growth retardation?," *Thrombosis Research*, 45:845–850 (1987).

(List continued on next page.)

Primary Examiner—Michael G. Wityshyn
Assistant Examiner—Nancy J. Degen
Attorney, Agent, or Firm—Richards, Medlock & Andrews

[57] ABSTRACT

It has been discovered that it is possible to administer truncated tissue factor (not having the transmembrane region) (tTF) in combination with factor VIIa (FVIIa) or an activator of endogenous factor VII to treat bleeding disorders such as those resulting from hemophilia or cirrhosis of the liver. The tTF is administered to produce up to 10 μg tTF/ml of plasma. The FVIIa or FVII activator is administered to produce levels of between 40 ng FVIIa/ml and 700 ng FVIIa/ml of plasma. The effective dosages of both tTF and FVIIa/factor VII activator are significantly and surprisingly less than the administration of either alone to stop bleeding. Examples demonstrate safety and efficacy in normal and hemophilic dogs.

19 Claims, 2 Drawing Sheets

DILUTE THROMBOPLASTIN CLOTTING TIME
Effect of tTF + fVIIa on clot time of normal plasma

OTHER PUBLICATIONS

Spicer, et al., "Isolation of cDNA clones coding for human tissue factor: primary structure of the protein cDNA," *Proc. Natl. Acad. Sci. USA*, 84:5148–5152 (1987).

Scarpati, et al., "Human tissue factor: cDNA sequence and chromosome localization of the gene," *Biochemistry*, 26:5234–5238 (1987).

Nemerson, "Tissue factor and hemostasis," *Blood*, 71:1–8 (1988).

Mackman, et al., "Complete sequence of the human tissue factor gene, a highly regulated cellular receptor that initiates the coagulation protease cascade," *Biochemistry*, 28:1755–1762 (1989).

Fisher, et al., "Cloning and expression of human tissue factor cDNA," *Thrombosis Research*, 48:89–99 (1987).

Zur, et al., "The dual role of Factor VII in blood coagulation," *J. Biol. Chem.*, 257:5623–5631 (1982).

Bach, et al., "Factor VII binding to tissue factor in reconstituted phospholipid vesicles: induction of cooperativity by phosphatidylserine," *Biochemistry*, 25:4007–4020 (1986).

Lawson, et al., "The evaluation of complex–dependent alterations in human Factor VIIa," *J. Biol. Chem.*, 267:4834–4843 (1992).

Giles, et al., "A combination of factor Xa and phosphatidylcholine-phosphatidylserine vesicles bypasses factor VIII in vivo", *British Journal of Haematology*, 1988, vol. 69, pp. 491–497, England.

Masys, et al., "Activation of Human Factor VII by Activated Factors IX and X", *Blood*, vol. 60, No. 5, pp. 1143–1150, Nov. 1982, U.S.A.

Radcliffe, et al., "Activation and Control of Factor VII by Activated Factor X and Thrombin," *The Journal of Biological Chemistry*, vol. 250, No. 2, Issue of Jan. 25, 1975, pp. 388–395, U.S.A.

Nakagaki, et al., "Activation of Human Factor VII by the Prothrombin Activator from the Venom of *Oxyuranus Scutellatus* (Taipan Snake)", *Thrombosis Research*, vol. 65; pp. 105–116, 1992, U.S.A.

Kisiel, et al., "Activation of Bovine Factor VII (Proconvertin) by Factor $XII_a$ (Activated Hageman Factor)", *Biochemistry*, vol. 16, No. 19, pp. 4189–4194, 1977, U.S.A.

Morrissey, et al., "Quantitation of Activated Factor VII Levels in Plasma Using a Tissue Factor Mutant Selectively Deficient in Promoting Factor VII Activation", *Blood*, vol. 81, No. 3, pp. 734–744, 1993, U.S.A.

Shigematsu, et al., "Expression of Human Soluble Tissue Factor in Yeast and Enzymatic Properties of Its Complex with Factor VIIa", *The Journal of Biological Chemistry*, vol. 267, No. 30, pp. 21329–21337, Issue of Oct. 25, 1992, U.S.A.

Seligsohn, et al., "Coupled Amidolytic Assay for Factor VII: Its Use with a Clotting Assay to Determine the Activity State of Factor VII", *Blood*, vol. 52, No. 5, pp. 978–988, Nov., 1978, U.S.A.

Rezaie, et al., "Expression and Purification of a Soluble Tissue Factor Fusion Protein with an Epitope for an Unusual Calcium–Dependent Antibody", *Protein Expression and Purification*, vol. 3, pp. 453–460, 1992, U.S.A.

Hedner, et al., "Use of Human Factor VIIa in the Treatment of Two Hemophilia A Patients with High–Titer Inhibitors", *Journal of Clinical Investigation*, vol. 71, pp. 1836–1841, Jun. 1983, U.S.A.

Telgt, et al., "Mechanism by which Recombinant Factor VIIa Shortens the aPTT: Activation of Factor X in the Absense of Tissue Factor", *Thrombosis Research*, vol. 56, pp. 603–609, 1989, U.S.A.

Brinkhous, et al., "Effect of recombinant factor VIIa on the hemostatic defect in dogs with hemophilia A, hemophilia B, and von Willebrand disease", *Proc. Natl. Aca. Sci.*, vol. 86, pp. 1382–1386, Feb. 1989, U.S.A.

Teitel, Jerome M., "The Factor VIII Bypassing Activity of Prothrombin Complex Concentrates: The Roles of VIIa and of Endothelial Cell Tissue Factor", *Thrombosis and Haemostasis*, vol. 66, No. 5, pp. 559–564, 1991, Stuttgart 1, Germany.

Hedner, Ulla, "Experiences with Recombinant Factor VIIa in Haemophiliacs", *Biotechnology of Plasma Proteins Curr. Stud. Hematol Blood Transf.*, No. 58, pp. 63–68, 1991, Basel, Switzerland.

O'Brien, et al., "Factor VIII–Bypassing Activity of Bovine Tissue Factor Using the Canine Hemophilic Model", *Journal of Clinical Investigation*, vol. 82, pp. 206–211, Jul. 1988, U.S.A.

Sakai, et al., "Formation of Tissue Factor Activity Following Incubation of Recombinant Human Tissue Factor Apoprotein with Plasma Lipoproteins", *Thrombosis Research*, vol. 60, pp. 213–222, 1990, U.S.A.

Brinkhous, et al., "Purified human factor VIII procoagulant protein: Comparative hemostatic response after infusions into hemophilic and von Willebrand disease dogs", *Proc. Natl. Acad. Sci.*, vol. 82, pp. 8752–8756, Dec. 1985, U.S.A.

Paborsky, et al., "Lipid Association, but Not the Transmembrane Domain, Is Required for Tissue Factor Activity", *The Journal of Biological Chemistry*, vol. 266, No. 32, pp. 21911–21916, 1991, U.S.A.

Morrissey, et al., "Monoclonal Antibody Analysis of Purified and Cell–Associated Tissue Factor", *Thrombosis Research*, vol. 52, pp. 247–261, 1988, U.S.A.

Fair, Daryl S., "Quantitation of Factor VII in the Plasma of Normal and Warfarin–Treated Individuals by Radioimmunoassay", *Blood*, vol. 62, No. 4, pp. 784–791, Oct. 1983, U.S.A.

Brinkhous, et al., "Pathophysiology of Platelet–Aggregating von Willebrand Factor: Applications of the Venom Coagglutinin vWF Assay", *Annals New York Acad. of Sciences*, vol. 370, pp. 191–204, 1981, U.S.A.

Hagen, et al., "Characterization of a cDNA coding for human factor VII", *Proc. Natl. Acad. Sci.*, vol. 83, pp. 2412–2416, Apr. 1986, U.S.A.

Graham, et al., "Canine Hemophilia", *J. Exp. Med.*, pp. 97–111, Mar. 1949, U.S.A.

Morrissey, et al., "Molecular Cloning of the cDNA for Tissue Factor, the Cellular Receptor for the Initiation of the Coagulation Protease Cascade", *Cell*, vol. 50, pp. 129–135, Jul. 1987, U.S.A.

Rehemtulla, et al., "The Isolated Extracellular Domain of Tissue Factor is Functional on Phospholipid Surfaces", *Thrombosis Haemostasis*, vol. 62, p. 347, 1989, Stuttgart 1, Germany.

Ruf, et al., "Phospholipid–independent and –dependent Interactions Required for Tissue Factor Receptor and Cofactor Function", *The Journal of Biological Chemistry*, vol. 266, pp. 2158–2166, 1991, U.S.A.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 795 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Homo sapiens
        ( F ) TISSUE TYPE: Fibroblast     ( i x ) FEATURE:
        ( A ) NAME/KEY: CDS
        ( B ) LOCATION: 34..786

( i x ) FEATURE:
        ( A ) NAME/KEY: mat_peptide
        ( B ) LOCATION: 130..786
        ( D ) OTHER INFORMATION: /product="Truncated Tissue Factor"

( x i ) SEQUENCE DESCRIPTION: SEQ ID NO:1:

```
CGTTCCGCTC GATCTCGCCG CCAACTGGTA GAC ATG GAG ACC CCT GCC TGG CCC        54
                                    Met Glu Thr Pro Ala Trp Pro
                                    -32         -30

CGG GTC CCG CGC CCC GAG ACC GCC GTC GCT CGG ACG CTC CTG CTC GGC        102
Arg Val Pro Arg Pro Glu Thr Ala Val Ala Arg Thr Leu Leu Leu Gly
-25              -20              -15               -10

TGG GTC TTC GCC CAG GTG GCC GGC GCT TCA GGC ACT ACA AAT ACT GTG        150
Trp Val Phe Ala Gln Val Ala Gly Ala Ser Gly Thr Thr Asn Thr Val
             -5                   1             5
```

| | | | | | | | | | | | | | | | | |
|---|---|---|---|---|---|---|---|---|---|---|---|---|---|---|---|---|
| GCA | GCA | TAT | AAT | TTA | ACT | TGG | AAA | TCA | ACT | AAT | TTC | AAG | ACA | ATT | TTG | 198 |
| Ala | Ala | Tyr | Asn | Leu | Thr | Trp | Lys | Ser | Thr | Asn | Phe | Lys | Thr | Ile | Leu | |
| | | | 10 | | | | 15 | | | | | 20 | | | | |
| GAG | TGG | GAA | CCC | AAA | CCC | GTC | AAT | CAA | GTC | TAC | ACT | GTT | CAA | ATA | AGC | 246 |
| Glu | Trp | Glu | Pro | Lys | Pro | Val | Asn | Gln | Val | Tyr | Thr | Val | Gln | Ile | Ser | |
| | 25 | | | | | 30 | | | | | 35 | | | | | |
| ACT | AAG | TCA | GGA | GAT | TGG | AAA | AGC | AAA | TGC | TTT | TAC | ACA | ACA | GAC | ACA | 294 |
| Thr | Lys | Ser | Gly | Asp | Trp | Lys | Ser | Lys | Cys | Phe | Tyr | Thr | Thr | Asp | Thr | |
| 40 | | | | | 45 | | | | 50 | | | | | | 55 | |
| GAG | TGT | GAC | CTC | ACC | GAC | GAG | ATT | GTG | AAG | GAT | GTG | AAG | CAG | ACG | TAC | 342 |
| Glu | Cys | Asp | Leu | Thr | Asp | Glu | Ile | Val | Lys | Asp | Val | Lys | Gln | Thr | Tyr | |
| | | | | 60 | | | | 65 | | | | | | 70 | | |
| TTG | GCA | CGG | GTC | TTC | TCC | TAC | CCG | GCA | GGG | AAT | GTG | GAG | AGC | ACC | GGT | 390 |
| Leu | Ala | Arg | Val | Phe | Ser | Tyr | Pro | Ala | Gly | Asn | Val | Glu | Ser | Thr | Gly | |
| | | | 75 | | | | | 80 | | | | | 85 | | | |
| TCT | GCT | GGG | GAG | CCT | CTG | TAT | GAG | AAC | TCC | CCA | GAG | TTC | ACA | CCT | TAC | 438 |
| Ser | Ala | Gly | Glu | Pro | Leu | Tyr | Glu | Asn | Ser | Pro | Glu | Phe | Thr | Pro | Tyr | |
| | | 90 | | | | | 95 | | | | | 100 | | | | |
| CTG | GAG | ACA | AAC | CTC | GGA | CAG | CCA | ACA | ATT | CAG | AGT | TTT | GAA | CAG | GTG | 486 |
| Leu | Glu | Thr | Asn | Leu | Gly | Gln | Pro | Thr | Ile | Gln | Ser | Phe | Glu | Gln | Val | |
| | 105 | | | | | 110 | | | | | 115 | | | | | |
| GGA | ACA | AAA | GTG | AAT | GTG | ACC | GTA | GAA | GAT | GAA | CGG | ACT | TTA | GTC | AGA | 534 |
| Gly | Thr | Lys | Val | Asn | Val | Thr | Val | Glu | Asp | Glu | Arg | Thr | Leu | Val | Arg | |
| 120 | | | | | 125 | | | | | 130 | | | | | 135 | |
| AGG | AAC | AAC | ACT | TTC | CTA | AGC | CTC | CGG | GAT | GTT | TTT | GGC | AAG | GAC | TTA | 582 |
| Arg | Asn | Asn | Thr | Phe | Leu | Ser | Leu | Arg | Asp | Val | Phe | Gly | Lys | Asp | Leu | |
| | | | | 140 | | | | 145 | | | | | | 150 | | |
| ATT | TAT | ACA | CTT | TAT | TAT | TGG | AAA | TCT | TCA | AGT | TCA | GGA | AAG | AAA | ACA | 630 |
| Ile | Tyr | Thr | Leu | Tyr | Tyr | Trp | Lys | Ser | Ser | Ser | Ser | Gly | Lys | Lys | Thr | |
| | | | 155 | | | | | 160 | | | | | 165 | | | |
| GCC | AAA | ACA | AAC | ACT | AAT | GAG | TTT | TTG | ATT | GAT | GTG | GAT | AAA | GGA | GAA | 678 |
| Ala | Lys | Thr | Asn | Thr | Asn | Glu | Phe | Leu | Ile | Asp | Val | Asp | Lys | Gly | Glu | |
| | | 170 | | | | | 175 | | | | | 180 | | | | |
| AAC | TAC | TGT | TTC | AGT | GTT | CAA | GCA | GTG | ATT | CCC | TCC | CGA | ACA | GTT | AAC | 726 |
| Asn | Tyr | Cys | Phe | Ser | Val | Gln | Ala | Val | Ile | Pro | Ser | Arg | Thr | Val | Asn | |
| | | 185 | | | | | 190 | | | | | 195 | | | | |
| CGG | AAG | AGT | ACA | GAC | AGC | CCG | GTA | GAG | TGT | ATG | GGC | CAG | GAG | AAA | GGG | 774 |
| Arg | Lys | Ser | Thr | Asp | Ser | Pro | Val | Glu | Cys | Met | Gly | Gln | Glu | Lys | Gly | |
| 200 | | | | | 205 | | | | | 210 | | | | | 215 | |
| GAA | TTT | AGA | GAA | TAAGAATTC | | | | | | | | | | | | 795 |
| Glu | Phe | Arg | Glu | | | | | | | | | | | | | |

( 2 ) INFORMATION FOR SEQ ID NO:2:

( i ) SEQUENCE CHARACTERISTICS:
( A ) LENGTH: 251 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Thr | Pro | Ala | Trp | Pro | Arg | Val | Pro | Arg | Pro | Glu | Thr | Ala | Val |
| -32 | | -30 | | | | | -25 | | | | | -20 | | | |
| Ala | Arg | Thr | Leu | Leu | Leu | Gly | Trp | Val | Phe | Ala | Gln | Val | Ala | Gly | Ala |
| | -15 | | | | | -10 | | | | | -5 | | | | |
| Ser | Gly | Thr | Thr | Asn | Thr | Val | Ala | Ala | Tyr | Asn | Leu | Thr | Trp | Lys | Ser |
| | 1 | | | | 5 | | | | | 10 | | | | | 15 |
| Thr | Asn | Phe | Lys | Thr | Ile | Leu | Glu | Trp | Glu | Pro | Lys | Pro | Val | Asn | Gln |
| | | | 20 | | | | | 25 | | | | | 30 | | |

| | | | | | | | | | | | | | | |
|---|---|---|---|---|---|---|---|---|---|---|---|---|---|---|
| Val | Tyr | Thr 35 | Val | Gln | Ile | Ser | Thr 40 | Lys | Ser | Gly | Asp 45 | Trp | Lys | Ser | Lys |
| Cys | Phe 50 | Tyr | Thr | Thr | Asp | Thr 55 | Glu | Cys | Asp | Leu | Thr 60 | Asp | Glu | Ile | Val |
| Lys 65 | Asp | Val | Lys | Gln | Thr 70 | Tyr | Leu | Ala | Arg | Val 75 | Phe | Ser | Tyr | Pro | Ala 80 |
| Gly | Asn | Val | Glu | Ser 85 | Thr | Gly | Ser | Ala | Gly 90 | Glu | Pro | Leu | Tyr | Glu 95 | Asn |
| Ser | Pro | Glu | Phe 100 | Thr | Pro | Tyr | Leu | Glu 105 | Thr | Asn | Leu | Gly | Gln 110 | Pro | Thr |
| Ile | Gln | Ser 115 | Phe | Glu | Gln | Val | Gly 120 | Thr | Lys | Val | Asn | Val 125 | Thr | Val | Glu |
| Asp | Glu 130 | Arg | Thr | Leu | Val | Arg 135 | Arg | Asn | Asn | Thr | Phe 140 | Leu | Ser | Leu | Arg |
| Asp 145 | Val | Phe | Gly | Lys | Asp 150 | Leu | Ile | Tyr | Thr | Leu 155 | Tyr | Tyr | Trp | Lys | Ser 160 |
| Ser | Ser | Ser | Gly | Lys 165 | Lys | Thr | Ala | Lys | Thr 170 | Asn | Thr | Asn | Glu | Phe 175 | Leu |
| Ile | Asp | Val | Asp 180 | Lys | Gly | Glu | Asn | Tyr 185 | Cys | Phe | Ser | Val | Gln 190 | Ala | Val |
| Ile | Pro | Ser 195 | Arg | Thr | Val | Asn | Arg 200 | Lys | Ser | Thr | Asp | Ser 205 | Pro | Val | Glu |
| Cys | Met 210 | Gly | Gln | Glu | Lys | Gly 215 | Glu | Phe | Arg | Glu | | | | | |

(2) INFORMATION FOR SEQ ID NO:3:

(i) SEQUENCE CHARACTERISTICS:
        (A) LENGTH: 1440 base pairs
        (B) TYPE: nucleic acid
        (C) STRANDEDNESS: double
        (D) TOPOLOGY: linear     (ii) MOLECULE TYPE: cDNA     (iii) HYPOTHETICAL: NO     (iv) ANTI-SENSE: NO     (vi) ORIGINAL SOURCE:
        (A) ORGANISM: Homo sapiens
        (F) TISSUE TYPE: Blood     (ix) FEATURE:
        (A) NAME/KEY: CDS
        (B) LOCATION: 36..1433
        (D) OTHER INFORMATION: /note="Coding portion of human factor VII cDNA"

(xi) SEQUENCE DESCRIPTION: SEQ ID NO:3:

```
TCAACAGGCA GGGGCAGCAC TGCAGAGATT TCATC ATG GTC TCC CAG GCC CTC         53
                                        Met Val Ser Gln Ala Leu
                                         1               5

AGG CTC CTC TGC CTT CTG CTT GGG CTT CAG GGC TGC CTG GCT GCA GGC       101
Arg Leu Leu Cys Leu Leu Leu Gly Leu Gln Gly Cys Leu Ala Ala Gly
             10                  15                  20

GGG GTC GCT AAG GCC TCA GGA GGA GAA ACA CGG GAC ATG CCG TGG AAG       149
Gly Val Ala Lys Ala Ser Gly Gly Glu Thr Arg Asp Met Pro Trp Lys
         25                  30                  35

CCG GGG CCT CAC AGA GTC TTC GTA ACC CAG GAG GAA GCC CAC GGC GTC       197
Pro Gly Pro His Arg Val Phe Val Thr Gln Glu Glu Ala His Gly Val
     40                  45                  50
```

| | | | | | | | | | | | | | | | | |
|---|---|---|---|---|---|---|---|---|---|---|---|---|---|---|---|---|
| CTG | CAC | CGG | CGC | CGG | CGC | GCC | AAC | GCG | TTC | CTG | GAG | GAG | CTG | CGG | CCG | 245 |
| Leu | His | Arg | Arg | Arg | Arg | Ala | Asn | Ala | Phe | Leu | Glu | Glu | Leu | Arg | Pro | |
| 55 | | | | 60 | | | | | 65 | | | | | 70 | | |
| GGC | TCC | CTG | GAG | AGG | GAG | TGC | AAG | GAG | GAG | CAG | TGC | TCC | TTC | GAG | GAG | 293 |
| Gly | Ser | Leu | Glu | Arg | Glu | Cys | Lys | Glu | Glu | Gln | Cys | Ser | Phe | Glu | Glu | |
| | | | | 75 | | | | 80 | | | | | 85 | | | |
| GCC | CGG | GAG | ATC | TTC | AAG | GAC | GCG | GAG | AGG | ACG | AAG | CTG | TTC | TGG | ATT | 341 |
| Ala | Arg | Glu | Ile | Phe | Lys | Asp | Ala | Glu | Arg | Thr | Lys | Leu | Phe | Trp | Ile | |
| | | | 90 | | | | | 95 | | | | | 100 | | | |
| TCT | TAC | AGT | GAT | GGG | GAC | CAG | TGT | GCC | TCA | AGT | CCA | TGC | CAG | AAT | GGG | 389 |
| Ser | Tyr | Ser | Asp | Gly | Asp | Gln | Cys | Ala | Ser | Ser | Pro | Cys | Gln | Asn | Gly | |
| | | 105 | | | | 110 | | | | | 115 | | | | | |
| GGC | TCC | TGC | AAG | GAC | CAG | CTC | CAG | TCC | TAT | ATC | TGC | TTC | TGC | CTC | CCT | 437 |
| Gly | Ser | Cys | Lys | Asp | Gln | Leu | Gln | Ser | Tyr | Ile | Cys | Phe | Cys | Leu | Pro | |
| | 120 | | | | 125 | | | | | 130 | | | | | | |
| GCC | TTC | GAG | GGC | CGG | AAC | TGT | GAG | ACG | CAC | AAG | GAT | GAC | CAG | CTG | ATC | 485 |
| Ala | Phe | Glu | Gly | Arg | Asn | Cys | Glu | Thr | His | Lys | Asp | Asp | Gln | Leu | Ile | |
| 135 | | | | | 140 | | | | 145 | | | | | 150 | | |
| TGT | GTG | AAC | GAG | AAC | GGC | GGC | TGT | GAG | CAG | TAC | TGC | AGT | GAC | CAC | ACG | 533 |
| Cys | Val | Asn | Glu | Asn | Gly | Gly | Cys | Glu | Gln | Tyr | Cys | Ser | Asp | His | Thr | |
| | | | | 155 | | | | 160 | | | | | 165 | | | |
| GGC | ACC | AAG | CGC | TCC | TGT | CGG | TGC | CAC | GAG | GGG | TAC | TCT | CTG | CTG | GCA | 581 |
| Gly | Thr | Lys | Arg | Ser | Cys | Arg | Cys | His | Glu | Gly | Tyr | Ser | Leu | Leu | Ala | |
| | | 170 | | | | 175 | | | | | 180 | | | | | |
| GAC | GGG | GTG | TCC | TGC | ACA | CCC | ACA | GTT | GAA | TAT | CCA | TGT | GGA | AAA | ATA | 629 |
| Asp | Gly | Val | Ser | Cys | Thr | Pro | Thr | Val | Glu | Tyr | Pro | Cys | Gly | Lys | Ile | |
| | | 185 | | | | 190 | | | | | 195 | | | | | |
| CCT | ATT | CTA | GAA | AAA | AGA | AAT | GCC | AGC | AAA | CCC | CAA | GGC | CGA | ATT | GTG | 677 |
| Pro | Ile | Leu | Glu | Lys | Arg | Asn | Ala | Ser | Lys | Pro | Gln | Gly | Arg | Ile | Val | |
| | 200 | | | | 205 | | | | | 210 | | | | | | |
| GGG | GGC | AAG | GTG | TGC | CCC | AAA | GGG | GAG | TGT | CCA | TGG | CAG | GTC | CTG | TTG | 725 |
| Gly | Gly | Lys | Val | Cys | Pro | Lys | Gly | Glu | Cys | Pro | Trp | Gln | Val | Leu | Leu | |
| 215 | | | | | 220 | | | | 225 | | | | | 230 | | |
| TTG | GTG | AAT | GGA | GCT | CAG | TTG | TGT | GGG | GGG | ACC | CTG | ATC | AAC | ACC | ATC | 773 |
| Leu | Val | Asn | Gly | Ala | Gln | Leu | Cys | Gly | Gly | Thr | Leu | Ile | Asn | Thr | Ile | |
| | | | | 235 | | | | 240 | | | | | 245 | | | |
| TGG | GTG | GTC | TCC | GCG | GCC | CAC | TGT | TTC | GAC | AAA | ATC | AAG | AAC | TGG | AGG | 821 |
| Trp | Val | Val | Ser | Ala | Ala | His | Cys | Phe | Asp | Lys | Ile | Lys | Asn | Trp | Arg | |
| | | | 250 | | | | 255 | | | | | 260 | | | | |
| AAC | CTG | ATC | GCG | GTG | CTG | GGC | GAG | CAC | GAC | CTC | AGC | GAG | CAC | GAC | GGG | 869 |
| Asn | Leu | Ile | Ala | Val | Leu | Gly | Glu | His | Asp | Leu | Ser | Glu | His | Asp | Gly | |
| | | 265 | | | | 270 | | | | | 275 | | | | | |
| GAT | GAG | CAG | AGC | CGG | CGG | GTG | GCG | CAG | GTC | ATC | ATC | CCC | AGC | ACG | TAC | 917 |
| Asp | Glu | Gln | Ser | Arg | Arg | Val | Ala | Gln | Val | Ile | Ile | Pro | Ser | Thr | Tyr | |
| 280 | | | | | 285 | | | | | 290 | | | | | | |
| GTC | CCG | GGC | ACC | ACC | AAC | CAC | GAC | ATC | GCG | CTG | CTC | CGC | CTG | CAC | CAG | 965 |
| Val | Pro | Gly | Thr | Thr | Asn | His | Asp | Ile | Ala | Leu | Leu | Arg | Leu | His | Gln | |
| 295 | | | | 300 | | | | | 305 | | | | | 310 | | |
| CCC | GTG | GTC | CTC | ACT | GAC | CAT | GTG | GTG | CCC | CTC | TGC | CTG | CCC | GAA | CGG | 1013 |
| Pro | Val | Val | Leu | Thr | Asp | His | Val | Val | Pro | Leu | Cys | Leu | Pro | Glu | Arg | |
| | | | | 315 | | | | 320 | | | | | 325 | | | |
| ACG | TTC | TCT | GAG | AGG | ACG | CTG | GCC | TTC | GTG | CGC | TTC | TCA | TTG | GTC | AGC | 1061 |
| Thr | Phe | Ser | Glu | Arg | Thr | Leu | Ala | Phe | Val | Arg | Phe | Ser | Leu | Val | Ser | |
| | | | 330 | | | | 335 | | | | | 340 | | | | |
| GGC | TGG | GGC | CAG | CTG | CTG | GAC | CGT | GGC | GCC | ACG | GCC | CTG | GAG | CTC | ATG | 1109 |
| Gly | Trp | Gly | Gln | Leu | Leu | Asp | Arg | Gly | Ala | Thr | Ala | Leu | Glu | Leu | Met | |
| | | 345 | | | | 350 | | | | | 355 | | | | | |
| GTG | CTC | AAC | GTG | CCC | CGG | CTG | ATG | ACC | CAG | GAC | TGC | CTG | CAG | CAG | TCA | 1157 |
| Val | Leu | Asn | Val | Pro | Arg | Leu | Met | Thr | Gln | Asp | Cys | Leu | Gln | Gln | Ser | |
| | 360 | | | | 365 | | | | | 370 | | | | | | |

| CGG Arg 375 | AAG Lys | GTG Val | GGA Gly | GAC Asp | TCC Ser 380 | CCA Pro | AAT Asn | ATC Ile | ACG Thr | GAG Glu 385 | TAC Tyr | ATG Met | TTC Phe | TGT Cys | GCC Ala 390 | 1205 |
| --- | --- | --- | --- | --- | --- | --- | --- | --- | --- | --- | --- | --- | --- | --- | --- | --- |
| GGC Gly | TAC Tyr | TCG Ser | GAT Asp | GGC Gly 395 | AGC Ser | AAG Lys | GAC Asp | TCC Ser | TGC Cys 400 | AAG Lys | GGG Gly | GAC Asp | AGT Ser | GGA Gly 405 | GGC Gly | 1253 |
| CCA Pro | CAT His | GCC Ala | ACC Thr | CAC His 410 | TAC Tyr | CGG Arg | GGC Gly | ACG Thr 415 | TGG Trp | TAC Tyr | CTG Leu | ACG Thr | GGC Gly 420 | ATC Ile | GTC Val | 1301 |
| AGC Ser | TGG Trp | GGC Gly | CAG Gln 425 | GGC Gly | TGC Cys | GCA Ala | ACC Thr | GTG Val 430 | GGC Gly | CAC His | TTT Phe | GGG Gly 435 | GTG Val | TAC Tyr | ACC Thr | 1349 |
| AGG Arg | GTC Val 440 | TCC Ser | CAG Gln | TAC Tyr | ATC Ile | GAG Glu 445 | TGG Trp | CTG Leu | CAA Gln | AAG Lys | CTC Leu 450 | ATG Met | CGC Arg | TCA Ser | GAG Glu | 1397 |
| CCA Pro 455 | CGC Arg | CCA Pro | GGA Gly | GTC Val | CTC Leu 460 | CTG Leu | CGA Arg | GCC Ala | CCA Pro | TTT Phe 465 | CCC Pro | TAGCCCA | | | | 1440 |

( 2 ) INFORMATION FOR SEQ ID NO:4:

( i ) SEQUENCE CHARACTERISTICS:
        ( A ) LENGTH: 466 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

| Met 1 | Val | Ser | Gln | Ala 5 | Leu | Arg | Leu | Leu | Cys 10 | Leu | Leu | Leu | Gly | Leu 15 | Gln |
| --- | --- | --- | --- | --- | --- | --- | --- | --- | --- | --- | --- | --- | --- | --- | --- |
| Gly | Cys | Leu | Ala 20 | Ala | Gly | Gly | Val | Ala 25 | Lys | Ala | Ser | Gly | Gly 30 | Glu | Thr |
| Arg | Asp | Met 35 | Pro | Trp | Lys | Pro | Gly 40 | Pro | His | Arg | Val | Phe 45 | Val | Thr | Gln |
| Glu | Glu 50 | Ala | His | Gly | Val | Leu 55 | His | Arg | Arg | Arg | Ala 60 | Asn | Ala | Phe | |
| Leu 65 | Glu | Glu | Leu | Arg | Pro 70 | Gly | Ser | Leu | Glu | Arg 75 | Glu | Cys | Lys | Glu | Glu 80 |
| Gln | Cys | Ser | Phe | Glu 85 | Glu | Ala | Arg | Glu | Ile 90 | Phe | Lys | Asp | Ala | Glu 95 | Arg |
| Thr | Lys | Leu | Phe 100 | Trp | Ile | Ser | Tyr | Ser 105 | Asp | Gly | Asp | Gln | Cys 110 | Ala | Ser |
| Ser | Pro | Cys 115 | Gln | Asn | Gly | Gly | Ser 120 | Cys | Lys | Asp | Gln | Leu 125 | Gln | Ser | Tyr |
| Ile | Cys 130 | Phe | Cys | Leu | Pro | Ala 135 | Phe | Glu | Gly | Arg | Asn 140 | Cys | Glu | Thr | His |
| Lys 145 | Asp | Asp | Gln | Leu | Ile 150 | Cys | Val | Asn | Glu | Asn 155 | Gly | Gly | Cys | Glu | Gln 160 |
| Tyr | Cys | Ser | Asp | His 165 | Thr | Gly | Thr | Lys | Arg 170 | Ser | Cys | Arg | Cys | His 175 | Glu |
| Gly | Tyr | Ser | Leu 180 | Leu | Ala | Asp | Gly | Val 185 | Ser | Cys | Thr | Pro | Thr 190 | Val | Glu |
| Tyr | Pro | Cys 195 | Gly | Lys | Ile | Pro | Ile 200 | Leu | Glu | Lys | Arg | Asn 205 | Ala | Ser | Lys |
| Pro | Gln 210 | Gly | Arg | Ile | Val | Gly 215 | Gly | Lys | Val | Cys | Pro 220 | Lys | Gly | Glu | Cys |
| Pro 225 | Trp | Gln | Val | Leu | Leu 230 | Leu | Val | Asn | Gly | Ala 235 | Gln | Leu | Cys | Gly | Gly 240 |

| | | | | | | | | | | | | | | |
|---|---|---|---|---|---|---|---|---|---|---|---|---|---|---|
| Thr | Leu | Ile | Asn | Thr 245 | Ile | Trp | Val | Val | Ser 250 | Ala | Ala | His | Cys | Phe 255 | Asp |
| Lys | Ile | Lys | Asn 260 | Trp | Arg | Asn | Leu | Ile 265 | Ala | Val | Leu | Gly | Glu 270 | His | Asp |
| Leu | Ser | Glu 275 | His | Asp | Gly | Asp | Glu 280 | Gln | Ser | Arg | Arg | Val 285 | Ala | Gln | Val |
| Ile | Ile 290 | Pro | Ser | Thr | Tyr | Val 295 | Pro | Gly | Thr | Thr | Asn 300 | His | Asp | Ile | Ala |
| Leu 305 | Leu | Arg | Leu | His | Gln 310 | Pro | Val | Val | Leu | Thr 315 | Asp | His | Val | Val | Pro 320 |
| Leu | Cys | Leu | Pro | Glu 325 | Arg | Thr | Phe | Ser | Glu 330 | Arg | Thr | Leu | Ala | Phe 335 | Val |
| Arg | Phe | Ser | Leu 340 | Val | Ser | Gly | Trp | Gly 345 | Gln | Leu | Leu | Asp | Arg 350 | Gly | Ala |
| Thr | Ala | Leu 355 | Glu | Leu | Met | Val | Leu 360 | Asn | Val | Pro | Arg | Leu 365 | Met | Thr | Gln |
| Asp | Cys 370 | Leu | Gln | Gln | Ser | Arg 375 | Lys | Val | Gly | Asp | Ser 380 | Pro | Asn | Ile | Thr |
| Glu 385 | Tyr | Met | Phe | Cys | Ala 390 | Gly | Tyr | Ser | Asp | Gly 395 | Ser | Lys | Asp | Ser | Cys 400 |
| Lys | Gly | Asp | Ser | Gly 405 | Gly | Pro | His | Ala | Thr 410 | His | Tyr | Arg | Gly | Thr 415 | Trp |
| Tyr | Leu | Thr | Gly 420 | Ile | Val | Ser | Trp | Gly 425 | Gln | Gly | Cys | Ala | Thr 430 | Val | Gly |
| His | Phe | Gly 435 | Val | Tyr | Thr | Arg | Val 440 | Ser | Gln | Tyr | Ile | Glu 445 | Trp | Leu | Gln |
| Lys | Leu 450 | Met | Arg | Ser | Glu | Pro 455 | Arg | Pro | Gly | Val | Leu 460 | Leu | Arg | Ala | Pro |
| Phe 465 | Pro | | | | | | | | | | | | | | |

TREATMENT OF BLEEDING WITH MODIFIED TISSUE FACTOR IN COMBINATION WITH AN ACTIVATOR OF FVII

The United States government has certain rights in this invention by virtue of grant R01 HL 44225 awarded by the National Institutes of Health to James H. Morrissey.

This is a continuation-in-part of U.S. Ser. No. 07/882,202, now U.S. Pat. No. 5,374,617 entitled "Treatment of Bleeding with Modified Tissue Factor in Combination with FVIIa" filed May 13, 1992 by James H. Morrissey and Philip C. Comp and a continuation-in-part of copending U.S. Ser. No. 07/683,682 entitled "Quantitative Clotting Assay for Activated Factor FVII" filed Apr. 10, 1991, by James H. Morrissey.

BACKGROUND OF THE INVENTION

Blood coagulation results from the production of thrombin, a proteolytic enzyme inducing platelet aggregation and cleaving fibrinogen to fibrin, which stabilizes the platelet plug. A number of proenzymes and procofactors circulating in the blood interact in this process through several stages during which they are sequentially or simultaneously converted to the activated form, ultimately resulting in the activation of prothrombin to thrombin by activated factor X (FXa) in the presence of factor Va, ionic calcium, and platelets.

Factor X can be activated by either of two pathways, termed the extrinsic and intrinsic pathways. The intrinsic pathway, or surface-mediated activation pathway, consists of a series of reactions where a protein precursor is cleaved to form an active protease, beginning with activation of factor XII to factor XIIa, which converts factor XI to factor XIa, which, in the presence of calcium, converts factor IX to factor IXa. Factors IX and X can also be activated via the extrinsic pathway by tissue factor (TF) in combination with activated factor VII (factor VIIa; FVIIa). Activated factor IX, in the presence of calcium, phospholipid (platelets), and factor VIIIa, activates factor X to factor Xa.

Physiologically, the major pathway involved in coagulation is believed to be the extrinsic pathway, an essential step of which is tissue factor-mediated activation of factor VII to factor VIIa. Tissue factor is an integral membrane glycoprotein having a protein and a phospholipid component. It has been isolated from a variety of tissues and species and reported to have a molecular mass of between 42,000 and 53,000. DNA encoding tissue factor and methods for expression of the protein have now been reported, for example, in European Patent Application 0 278 776 by Genentech, Inc. and by J. H. Morrissey, et al. *Cell* 50, 129–135 (1987).

The complex of factor VIIa and its essential cofactor, TF, is the most potent known trigger of the clotting cascade. Factor VII is present in plasma at a concentration of 0.5 µg/ml plasma. In contrast, factor VIIa is present in plasma at trace levels of roughly 1 ng/ml. Accordingly, factor VII is normally in considerable excess over factor VIIa. Factor VIIa circulates with a relatively long half-life of about two hours in plasma. This is an unusual property among activated coagulation enzymes, which typically are inactivated very rapidly by various protease inhibitors in plasma.

Hemophilia A is characterized by the absence of active coagulation factor VIII or the presence of inhibitors to factor VIII. Hemophilia B is characterized by the absence of active factor IX. Both types of hemophilia are associated with bleeding diatheses that can lead to crippling injuries or death. Traditionally, patients with either type of hemophilia were treated with infusion of plasma concentrates to stop bleeding episodes. The problems with the concentrates are many, especially infection, most recently with HIV. Highly purified factor VIII or factor IX have been introduced to obviate these problems, as have methods of treating factor concentrates to inactivate viruses. However, some patients develop high-titer, inhibitory antibodies to factor VIII. Therefore, such patients can no longer be treated with conventional factor VIII replacement therapy.

As described by Hedner and Kisiel, *J. Clin. Invest.* 71, 1836–1841 (1983), purified naturally produced factor VIIa can be administered to hemophilia A patients with high titers of antibodies against factor VIII:C and restore hemostasis in these patients. As reported by Brinkhous, et al., *Proc. Natl. Acad. Sci. USA* 86, 1382–1386 (1989), recombinant factor (rFVIIa) can be administered to hemophilic and von Willebrand disease dogs and stop bleeding in both hemophilic A and B dogs, but not the von Willebrand disease dogs. Telgt, et al., *Thrombosis Res.* 56, 603–609 (1989), reported that, at high levels, rFVIIa was believed to act by direct activation of factor X, in the presence of calcium and phospholipid but in the absence of TF. Teitel, *Thrombosis and Haemostasis* 66(5), 559–564 (1991), reported that the important ingredient in prothrombin complex concentrates for efficacy in treating hemophilia is factor VIIa.

Hedner, "Experiences with Recombinant Factor VIIa in Haemophiliacs" in *Biotechnology of Plasma Proteins* Lenfant, Mannucci, Sixma, eds., *Curr. Stud. Hematol. Blood Transf.* No. 58, 63–68 (1991), review the use of prothrombin complex concentrates (effective in only 50 to 60% of the bleeds), as well as the use of plasma-derived (pFVIIa) and recombinant factor VIIa (rFVIIa). Dosages of 10 to 15 µg/kg of pFVIIa were effective in some hemophilia A patients. Safety studies in dogs and rabbits indicated that the recombinant factor VIIa was safe and efficacious at dosages of up to 150 µg/kg. A number of patients were also successfully treated, using dosages of between 54 µg/kg and 90 µg/kg during surgery and bleeding complications. Gringeri, et al., reported that treatment of hemophiliacs with rFVIIa is not always effective, even at dosages of 75 µg/kg at intervals of every two to three hours. The authors noted that perhaps larger dosages, more frequent infusions, and/or the concomitant use of antifibrinolytic medication might be required in such cases. rFVIIa is currently in clinical trials in the United States for treatment of hemophilia, particularly hemophilia in patients with inhibitors who do not benefit from conventional factor VIII or factor IX replacement therapy. Doses of rFVIIa currently employed are typically 45 to 90 µg rFVIIa/kg body weight, and are repeated every two to four hours. These doses are designed to achieve a level of circulating rFVIIa of approximately 4 µg/ml, extremely high compared to the normal plasma concentrations of FVII of approximately 0.5 µg/ml or FVIIa of approximately 1 ng/ml.

O'Brien, et al., *J. Clin. Invest.* 82, 206–211 (1988), reported that apo-TF, a delipidated preparation of the normally lipid-associated TF glycoprotein could be used to normalize bleeding in animals having antibodies to factor VIII. Since purified apo-TF is inactive unless incorporated into a phospholipid membrane, the theoretical basis for infusing apo-TF is the hypothesis that it would spontaneously and preferentially incorporate into exposed membrane surfaces, particularly into damaged cells at the sites of injury. Subsequent studies have indicated there are dangers associated with the use of purified apo-TF in the treatment of hemophilia. The apo-TF can spontaneously incorporate into many types of lipid membranes and become active at sites where clotting is not desired, resulting in thrombosis or disseminated intravascular coagulation (DIC). Indeed, O'Brien, et al., reported evidence of DIC in some animals receiving apo-TF, and Sakai and Kisiel, *Thromb. Res.* 60, 213–222 (1990), recently demonstrated that apo-TF will spontaneously combine with plasma lipoproteins to form active TF. This latter phenomenon is cause for concern because of a number of studies which have demonstrated that intravenous administration of active TF is a potent inducer of DIC.

Recently, a soluble, truncated form of TF (tTF) has been reported which retains some cofactor function towards factor VIIa as measured in vitro using purified proteins. However, this form of TF has been dismissed as an alternative to TF because it has almost no procoagulant activity when tested with normal plasma, as reported by Paborsky, et al., *J. Biol. Chem.* 266:21911–21916 (1991).

As described in U.S. Ser. No. 07/683,682 entitled "Quantitative Clotting Assay for Activated Factor VII" filed Apr. 10, 1991 by James H. Morrissey, the reason tTF was reported to lack procoagulant activity in the prior art is because, although tTF retains cofactor function toward factor VIIa, tTF had lost the ability to promote conversion of factor VII to factor VIIa. As a consequence, tTF can clot plasma only in conjunction with significantly elevated levels of factor VIIa, as compared to normal plasma, which contains only trace levels of factor VIIa.

It is therefore an object of the present invention to provide a method and composition for treatment of significant bleeding disorders, such as hemophilia, including those hemophiliacs with high titers of anti-factor VIII antibodies.

It is a further object of the present invention to provide a method and compositions for treatment of patients with bleeding disorders that are relatively safe and can be produced in commercial quantities.

SUMMARY OF THE INVENTION

It has been discovered that it is possible to administer truncated tissue factor (the isolated extracellular domain of tissue factor) (tTF) in combination with factor VIIa (FVIIa), or truncated tissue factor in combination with an activator of factor VII such as the combination of factor Xa/phospholipid, factor IXa/phospholipid, thrombin, factor XIIa, or the factor VII activator from the venom of *Oxyuranus scutellatus*/phospholipid, to treat bleeding disorders such as, for example, those associated with hemophilia or cirrhosis of the liver. The tTF is administered to produce up to 10 μg tTF/ml of plasma. The FVIIa, or composition to activate endogenous FVII to form FVIIa, is administered to produce levels of between 40 ng FVIIa/ml and 700μ FVIIa/ml of plasma. In the case of addition of an activator of FVIIa, the maximum achievable level of FVIIa is expected to be about 700 nanograms per milliliter of plasma, depending on the level of endogenous FVII. The minimal effective dosages of both tTF and FVIIa are significantly and surprisingly less than the administration of either alone to stop bleeding.

Examples demonstrate safety and efficacy in normal and hemophilic dogs.

DETAILED DESCRIPTION OF THE INVENTION

Truncated tissue factor (tTF) is used as an adjuvant for factor VIIa (FVIIa) therapy of excessive bleeding in patients such as hemophiliacs. The tTF is administered in combination with either the FVIIa or a composition which activates endogenous FVII to form FVIIa (such as the combination of FXa and phospholipid), or it is administered immediately before or after the FVIIa or FVII activator. As used herein, "FVIIa" refers to administration of either FVIIa or an activator of FVII to FVIIa. The minimal effective dosage of FVIIa is significantly decreased by the tTF, while the thrombogenicity of the mixture is reduced as compared to a mixture of FVIIa and TF in its native form.

The advantage, and necessity, of using a combination of FVIIa plus tTF over tTF alone is that tTF is active in promoting blood clotting only in the presence of pre-formed FVIIa. The advantage of using the combination of FVIIa plus tTF over FVIIa alone is that FVIIa is approximately 22-fold more potent at clotting plasma in the presence of tTF than in the absence of tTF. Furthermore, as with FVIIa alone, the complex of tTF plus FVIIa activates factor X at markedly enhanced rates in the presence of negatively charged phospholipids such as phophatidyl serine, even though tTF is not itself incorporated into lipid membranes. Normally, negatively charged phospholipids are sequestered into the inner leaflet of the plasma membrane of cells, and thus are not exposed to the cell surface unless the cells are damaged, or, in the case of platelets, the platelets have undergone surface activation. Thus, negatively charged phospholipids should be preferentially exposed on cell surfaces at anatomic sites that have experienced trauma sufficient to cause cell lysis and/or platelet activation. This means that the complex of tTF and FVIIa is predicted from in vitro studies to be active in promoting blood clotting preferentially at sites of injury, where it would be needed to confer hemostasis. Furthermore, tTF, by itself or in complex with FVIIa, remains a soluble entity and does not become incorporated into lipid membranes. This means that it should clear relatively rapidly from the circulation, diminishing the risk of thrombosis. Because of these properties, the complex of tTF and FVIIa should not cause systemic activation of the blood clotting system leading to DIC, as can injection of wild-type TF. These in vitro results are consistent with results from in vivo studies in normal and hemophiliac dogs described below.

The combination of tTF plus FVIIa should be useful for treatment of hemophilia A, hemophilia B, congenital or acquired deficiencies in any other blood coagulation factor, or platelet defects. Other patients that can be treated with the combination include patients suffering from severe trauma, postoperative bleeding or those with cirrhosis.

Truncated Tissue Factor

As used herein, "truncated tissue factor" is a soluble tissue factor having only the extracellular domains, which is not bound to a phospholipid membrane surface, and therefore does not support conversion of FVII to FVIIa, as described in U.S. Ser. No. 07/683,682 filed Apr. 10, 1991, the teachings of which are incorporated herein. In the preferred embodiment, truncated tissue factor is a recombinant protein produced in vitro in cell culture using a mammalian cell line such as CHO-K1 cells, American Type Culture Collection CCL 61. These cells are stably transfected with a mutant form of the human tissue factor cDNA carried in a commercially available expression vector, and secrete a form of tissue factor consisting only of amino acids 1– 219 (numbered according to Morrissey, et al., *Cell* 50:129–135 (1987), the teachings of which are incorporated herein).

The recombinant, truncated tissue factor is purified from the culture medium using an immobilized monoclonal antibody to human tissue factor, such as TF9-5B7, described in Morrissey, et al. *Thromb. Res.* 52:247–261 (1988). Hybridomas for production of monoclonal antibodies can be propagated by ascites growth and the monoclonal antibodies (MAbs) purified from ascites fluid using the BioRad MAPS II system for mAb purification, as described by Morrissey, et al., *Thromb. Res.* 52:247–261 (1988).

The TF9-5B7 is coupled to Affigel™ beads. Detergent is not used during the purification of $TF_{219}$. After removal of cellular debris by centrifugation, the culture medium is made 25 mM in Tris.HCl (pH 7.4), 10 mM in sodium EDTA (pH 7.4), and 0.1% in sodium azide by the addition of concentrated stock solutions. In order to remove proteins that bind to agarose beads non-specifically, the culture medium is gently agitated for 4 hr at 4° C. with AffiGel™-10 beads that had previously been blocked chemically with glycine ethyl ester (GEE-AffiGel). The GEE-AffiGel beads are removed by filtration through a sintered glass funnel, and the supernatant is agitated overnight at 4° C. with the MAb TF9-5B7 coupled to AffiGel beads (typically 2 ml of beads). The TF9-5B7-AffiGel beads are collected on a sintered glass funnel, and the beads are washed on the funnel with 100 ml of TBS-EDTA (TBS=100 mM NaCl, 50 mM Tris.HCl (pH 7.4), and 0.02% sodium azide; TBS-EDTA=TBS with 10 mM EDTA included). The beads are then transferred to a chromatography column and washed with 40 ml TBS followed by 40 ml of a solution consisting of 1M NaCl, 10 mM Tris.HCl (pH 7.4), and 0.02% sodium azide. Truncated TF is eluted from the beads using 100 mM glycine. HCl (pH 2.5), with 1 ml fractions being collected into tubes containing 57 µl 1M Tris base (to immediately neutralize the acidic glycine buffer). Fractions containing protein are detected using the BCA protein assay (Pierce), pooled, dialyzed against TBS, and then stored at −70° C. Protein concentrations are determined using standard methods such as the BCA assay (Pierce Chemical Co.) based on a bovine serum albumin standard of known concentration.

For production of recombinant truncated TF, cells are typically grown to confluence in roller bottles in Dulbecco's Modified Eagle's Medium (DMEM) supplemented with 10% iron-supplemented calf serum (HyClone Laboratories, Logan, Utah). Upon reaching confluence, the cultures are shifted to DMEM containing 2% serum, and culture medium is collected every four days thereafter.

The nucleotide and amino acid sequence of truncated tissue factor (tTF) is shown below as SEQ ID NO:1 and SEQ ID NO:2, respectively. The truncated tissue factor protein lacks the predicted transmembrane and cytoplasmic domains of tissue factor. This version of the protein retains cofactor activity, as reported by Ruf, et al., *Thromb. Haemost.* 62, 347 (abstract) 1079 (1989) and Ruf, et al., *J. Biol. Chem.* 266:2158–2166 (1991). This truncated form of tissue factor fails to support conversion of factor VII to VIIa, allowing it to be used in a specific clotting assay for factor VIIa free from interference by factor VII.

Since the vast majority of FVII in plasma is in the inactive, zymogen form, and since tTF is selectively deficient in promoting conversion of factor VII to FVIIa, tTF has extremely little procoagulant activity towards normal plasma. Since tTF lacks the membrane-anchoring domain of the protein, it lacks the ability to become incorporated into exposed phospholipid surfaces as wild-type apo-TF can. Although the deficiency of tTF in the conversion of FVII to FVIIa was not previously appreciated, its extremely low procoagulant activity when tested with normal plasma has made it appear to be unacceptable as a therapeutic agent to control bleeding in hemophilia.

The essential difference between truncated tissue factor and wild-type tissue factor is that truncated tissue factor is no longer tethered to the phospholipid membrane surface. It is therefore expected that other methods for preparing truncated tissue factor can be used to generate an essentially equivalent soluble form of tissue factor that retains FVIIa cofactor activity while no longer stimulating conversion of factor VII to factor VIIa. Methods include chemical and/or enzymatic cleavage of wild-type tissue factor to separate the predicted extracellular domain from the transmembrane region. Recombinant human TF is available from Calbiochem Corporation. Precise positioning of the stop codon following amino acid 219 is believed to not be essential to make functional truncated TF, and other placements of a stop codon near amino acid 219 are predicted to yield an essentially equivalent product with respect to its ability in conjugation with FVIIa to serve as a treatment for bleeding disorders.

Activated Factor VII

Factor VII can be prepared as described by Fair, *Blood* 62, 784–791 (1983). The coding portion of the human factor VII cDNA sequence reported by Hagen et al., *Proc. Natl. Acad. Sci. USA* 83:2412–2416 (1986) is shown below as SEQ ID NO:3, along with the translated amino acid sequence, SEQ ID NO:4. The amino acid sequence from 1 to 60 corresponds to the pre-pro/leader sequence that is removed by the cell prior to secretion. The mature FVII polypeptide chain consists of amino acids 61 to 466. FVII is converted to FVIIa by cleavage of a single peptide bond between arginine-212 and isoleucine-213.

FVII can be converted in vitro to FVIIa by incubation of the purified protein with factor Xa immobilized on Affi-Gel™ 15 beads (Bio-Rad). Conversion can be monitored by SDS-polyacrylamide gel electrophoresis of reduced samples. Free factor Xa in the FVIIa preparation can be detected with the chromogenic substrate methoxycarbonyl-D-cyclohexylglycyl-glycylarginine-p-nitroanilide acetate (Spectrozyme™ FXa, American Diagnostica, Greenwich, Conn.) at 0.2 mM final concentration in the presence of 50 mM EDTA.

Recombinant FVIIa can also be purchased from Novo Biolabs (Danbury, Conn.).

Formation of FVIIa in vivo

Alternatively, the FVIIa can be formed in vivo, at the time of, or shortly before, administration of the truncated tissue factor. In a preferred embodiment, endogenous FVII is converted into FVIIa by infusion of an activator of FVIIa, such as factor Xa (FXa) in combination with phospholipid (PCPS).

Activators of factor VII in vivo include FXa/PCPS, FIXa/PCPS, thrombin, FXIIa, and the FVII activator from the venom of *Oxyuranus scutellatus* in combination with PCPS. These have been shown to activate FVII to FVIIa in vitro, although never in combination with truncated tissue factor:

FXa and Thrombin: Radcliffe, R. and Nemerson, Y. (1975). Activation and control of factor VII by activated factor X and thrombin: Isolation and characterization of a single chain form of factor VII. *J. Biol. Chem.* 250:388–395. This paper points out that activation of FVII by FXa is accelerated when phospholipids are present.

FIXa and FXa: Masys, D. R., Bjaj, S. P. and Rapaport, S. I. (1982). Activation of human factor VII by activated factors IX and X. *Blood* 60:1143–1150. This paper describes activation of factor VII by both factors IXa and Xa, and the fact that phospholipids accelerate both reactions.

FXa plus phospholipids in vivo: Giles, A. R., Mann, K. G. and Nesheim, M. E. (1988). A combination of factor Xa and phosphatidylcholine-phosphatidylserine vesicles bypasses factor VIII in vivo. *Br. J. Haematol.* 69:491–497. This paper describes the factor VIII bypassing activity of FXa/PCPS in hemophilic dogs. It does not deal with activation of factor VII.

FXIIa: Kisiel, W., Fujikawa, K. and Davis, E. W. (1977). Activation of bovine factor VII (proconvertin) by factor XIIa (activated Hagsman factor). *Biochemistry* 16:4189–4194. Describes activation of bovine FVII by FXIIa (no phospholipids).

Snake venom activator of FVII: Nakagaki, T., Lin, P. and Kisiel, W. (1992). Activation of human factor VII by the prothrombin activator from the venom of *Oxyuranus scutellatus* (Taipan snake). *Thromb. Res.* 65:105–116. This paper describes the isolation of an enzyme from this snake venom which, in combination with phospholipids, will activate factor VII to VIIa in vitro.

Activation of FVII to FVIIa for Xa/PCPS in vivo has also been measured directly.

In general, the factor VII activator is administered in a dosage between 1 and 10 μg/ml of carrier.

The phospholipid can be provided in a number of forms but the preferred form is as phosphatidyl choline/phosphatidyl serine vesicles (PCPS). The PCPS vesicle preparations and the method of administration of Xa/PCPS is described in Giles, et al., (1988), the teachings of which are specifically incorporated herein. Other phospholipid preparations can be substituted for PCPS, so long as they accelerate the activation of FVII by FXa. Effectiveness, and therefore determination of optimal composition and dose, can be monitored as described below.

A highly effective dose of Xa/PCPS, which elevates FVIIa levels in vivo in the chimpanzee, was 26 pmoles FXa+40 pmoles PCPS per kg body weight. That dose yielded an eighteen fold increase in endogenous levels of FVIIa (to 146 ng/ml). A marginally detectable effect was observed using a smaller dose in dogs, where the infusion of 12 pmoles FXa+19 pmoles PCPS per kg body weight yielded a three fold increase in endogenous FVIIa levels. Accordingly, doses of FXa that are at least 12 pmoles FXa per kg body weight, and preferably 26 pmoles FXa per kg body weight, should be useful. Doses of PCPS that are at least 19 pmoles PCPS per kg body weight, and preferably 40 pmoles PCPS per kg body weight, are similarly useful.

The effectiveness of any infusible FVII activator can be monitored, following intravenous administration, by drawing citrated blood samples at varying times (at 2, 5, 10, 20, 30, 60, 90 and 120 min) following a bolus infusion of the activator, and preparing platelet-poor plasma from the blood samples. The amount of endogenous FVIIa can then be measured in the citrated plasma samples by performing our tTF-based FVIIa clotting assay. Desired levels of endogenous FVIIa would be the same as the target levels of plasma FVIIa indicated for co-infusion of purified FVII and tTFo Therefore, other activators of FVII could be tested in vivo for generation of FVIIa, without undue experimentation, and the dose adjusted to generate the desirable levels of FVIIa, using the tTF-based FVIIa assay of plasma samples. The proper dose of the FVII activator (yielding the desired level of endogenous FVIIa) can then be used in combination with the recommended amounts of tTF.

Doses can be timed to provide prolong elevation in FVIIa levels. Preferably doses would be administered every two hours until the desired hemostatic effect is achieved, and then repeated as needed to control bleeding. The half-life of FVIIa in vivo has been reported to be approximately two hours, although this could vary with different therapeutic modalities and individual patients. Therefore, the half-life of FVIIa in the plasma in a given treatment modality should be determined with the tTF-based clotting assay.

Administration of the combination of the tTF and FVIIa

The tTF and FVIIa are administered by infusion in the preferred embodiment, using a pharmaceutically acceptable carrier such as saline or buffered saline. The tTF and FVIIa can also be administered topically either by direct application using a conventional topical base such as petrolatum or a water based gel, or as an aerosol spray.

The tTF is administered in a dosage effective to produce in the plasma an effective level of between 100 ng/ml and 50 μg/ml, or a preferred level of between 1 μg/ml and 10 μg/ml or 60 to 600 μg/kg body weight, when administered systemically; or an effective level of between 10 μg/ml and 50 μg/ml, or a preferred level of between 10 μg/ml and 50 μg/ml, when administered topically.

The FVIIa is administered in a dosage effective to produce in the plasma an effective level of between 20 ng/ml and 10 μg/ml, (1.2 to 600 μg/kg), or a preferred level of between 40 ng/ml and 700 μg/ml (2.4 to 240 μg/kg), or a level of between 1 μg FVIIa/ml and 10 μg FVIIa/ml when administered topically.

In general, one would administer tTF and FVII activator to produce levels of up to 10 μg tTF/ml plasma and between 40 ng and 700 μg FVIIa/ml plasma. For hemophilic patients, one would administer tTF and FVIIa to produce levels of up to 10 μg tTF and between 100 and 300 ng FVIIa/ml. For patients with cirrhosis, one would administer the same amount of tTF but up to 1 μg FVIIa/ml plasma.

The FVII activator is administered in a dosage effective to produce in the plasma an effective level of FVIIa, as defined above.

Since tTF cannot stimulate conversion of FVII to FVIIa, it should only be functional in conjunction with elevated factor VIIa levels. Therefore, tTF is expected to be an effective hemostatic agent only in association with FVIIa therapy or in individuals who have elevated FVIIa levels for some other reason.

Other conditions that can be treated with this combination include surgical bleeding from the microvasculature, bleeding at skin graft harvest sites, postoperative bleeding, including following orthopedic surgery, brain surgery or brain trauma, bleeding secondary to thrombocytopenia, and platelet dysfunction.

EXAMPLE 1

Safety of tTF and FVIIa in normal dogs.

Three beagle dogs were treated with either tTF or tTF plus FVIIa.

Dog #5533 was treated with tTF alone, in a dosage of 60 μg tTF/kg body weight by intravenous bolus infusion.

ELISA studies showed 1.23 μg tTF/ml in plasma at time zero. Half-life of tTF was 2.2 hr in this dog.

Dog #5534 was also treated with tTF alone, in a dosage of 41 μg tTF/kg body weight by intravenous bolus infusion. Assuming a blood volume of 60 ml/kg, this should have produced a level of 0.67 μg tTF/ml in the blood. ELISA studies showed 0.60 μg tTF/ml in plasma at time zero. Half-life of tTF was 1.3 hr in this dog.

Dog #5734 was treated with tTF in combination with FVIIa, in a dosage of 41 μg tTF/kg body weight and 6.37 μg Novo recombinant factor VIIa/kg body weight by intravenous bolus infusion. ELISA studies showed 0.51 μg tTF/ml in plasma at time zero. Half-life of tTF was biphasic (1 hr followed by 3.0 hr) in this dog.

The dogs all remained healthy and active. Blood tests of the clotting system indicated no significant decrease in fibrinogen levels or platelet counts and no measurable increase in fibrin degradation products. Prothrombin times and APTT times were normal, as were white blood cell counts, and red blood cell counts. Therefore, administration of either tTF alone, or tTF in conjunction with FVIIa, caused no measurable disseminated intravascular coagulation or other detectable coagulopathy.

A complete necropsy was performed on the animal receiving truncated tissue factor and factor VIIa. No evidence of thrombosis was found in veins, arteries or in the capillaries. There was no evidence on gross and microscopic examination of myocardial infarction or of cerebral infarction (stroke).

EXAMPLE 2

In vitro correction of clotting time of hemophilic plasma with tTF in combination with FVIIa.

A modified prothrombin test (PT) was performed with diluted thromboplastin (since hemophiliacs have normal PT's unless the thromboplastin is diluted) using either normal or congenital factor VIII deficient (Hemophilia A) plasma. Sigma Chemical Co. rabbit brain thromboplastin was diluted 1:500 with TBS/0.1% BSA/rabbit brain cephalin (Sigma Chemical Co.).

12×75 mm glass test tubes were pre-warmed in a 37° C. water bath.

Diluted thromboplastin was added (0.1 ml) and allowed to warm to 37° C. for more than two minutes.

Plasma sample (0.1 ml) was added and allowed to warm to exactly 30 sec.

Pre-warmed 25 mM $CaCl_2$ (at 37° C.) was added and the clotting time was determined by the manual tilt-tube method.

Figure 1A:
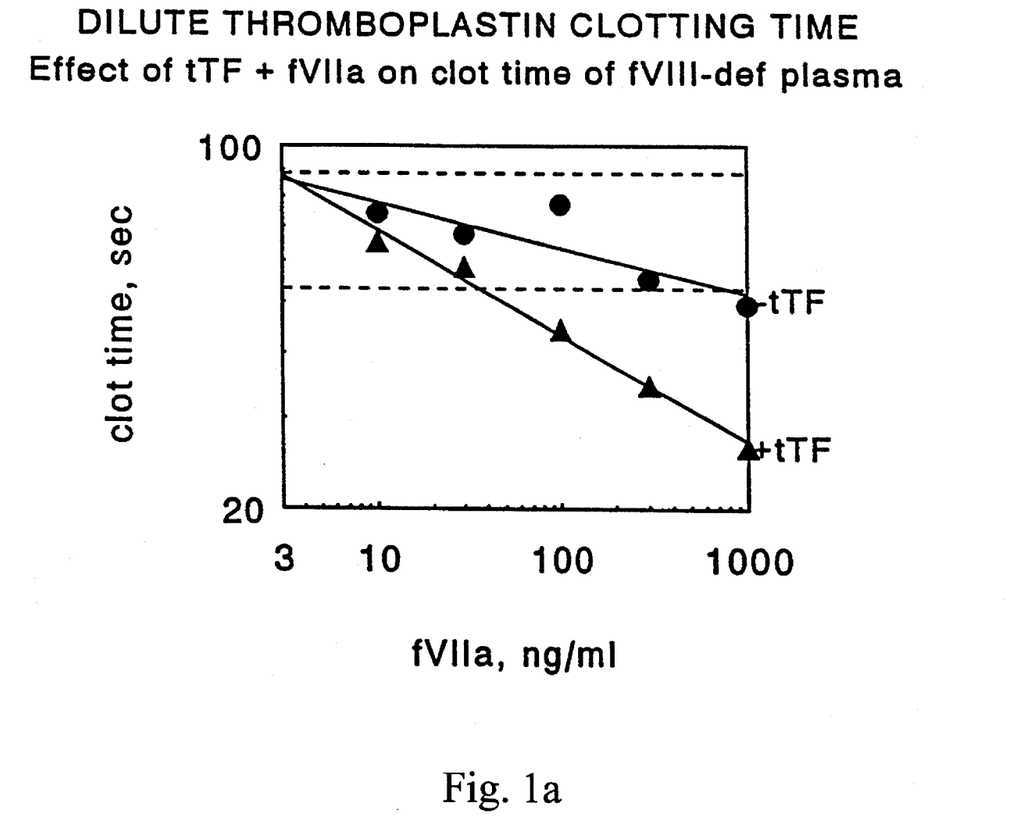
FIG. 1a is a graph of dilute thromboplastin clotting time (seconds) for factor VIII-deficient plasma when tTF and FVIIa (ng/ml) are added (dark triangles) or when FVIIa alone (ng/ml) are added (dark circles).
Figure 1B:
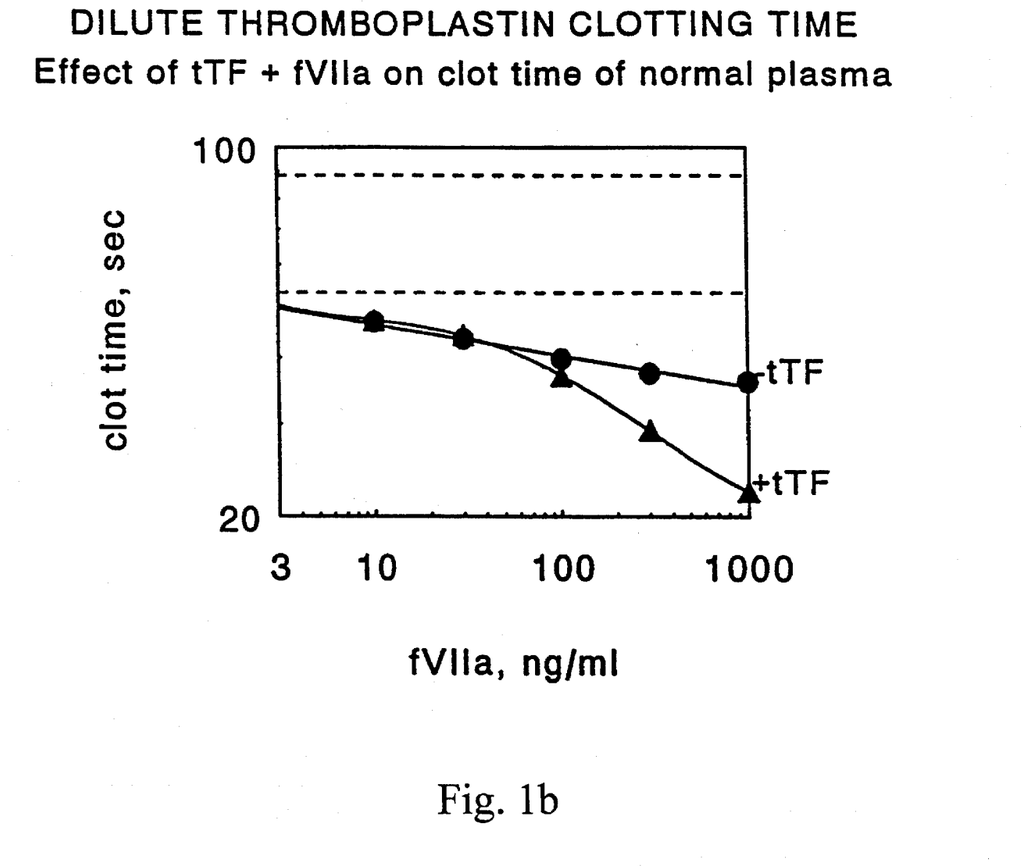
FIG. 1b is a graph of dilute thromboplastin clotting time (seconds) for normal plasma when tTF and FVIIa (ng/ml) are added (dark triangles) or when FVIIa alone (ng/ml) are added (dark circles).

The results are shown in FIG. 1a and b. FIG. 1a is a graph of dilute thromboplastin clotting time (seconds) for factor VIII-deficient plasma when tTF (1 μg/ml) and varying concentrations of FVIIa (ng/ml) are added (dark triangles) or when varying concentrations of FVIIa alone (ng/ml) are added (dark circles). FIG. 1b is a graph of dilute thromboplastin clotting time (seconds) for normal plasma when tTF (1 μg/ml) and varying concentrations FVIIa (ng/ml) are added (dark triangles) or when varying concentration of FVIIa alone (ng/ml) are added (dark circles). The clotting time of the hemophilic plasma without any added FVIIa or tTF was 88.5 sec which is indicated by the upper dotted horizontal line. The clotting time of normal plasma without added FVIIa or tTF was 53.0 sec which is indicated by the lower dotted horizontal line. Without added tTF, the 88.5 sec clotting time of the hemophilic plasma was reduced to that of normal plasma (53 sec) at 808 ng FVIIa/ml of plasma. With added tTF (at 1 μg/ml), the clotting time of the hemophilic plasma was reduced to that of normal plasma at 36.8 ng FVIIa/ml plasma.

Therefore, in the presence of 1 μg/ml tTF in plasma, correction of the prolonged clotting time of hemophilic plasma was achieved at a level of added FVIIa that was 22-fold lower than in the absence of added tTF. In addition, tTF was not able to correct the prolonged clotting time of hemophilic plasma in the absence of added FVIIa.

EXAMPLE 3

Efficacy of the combination of tTF and FVIIa in the treatment of Hemophilic Dogs.

As described by Brinkhous, et al., *Proc. Natl. Acad. Sci. USA* 82, 8752–8756 (1985), Graham, et al., *J. Exp. Med.* 90, 97–111 (1949), and Brinkhous, et al., *Ann. N.Y. Acad. Sci.* 370, 191–204 (1981), a colony of hemophilic dogs has been developed at the University of North Carolina at Chapel Hill. Dogs have hemophilia A. A test (secondary cuticle bleeding time) is used to measure bleeding tendency.

A modified toenail bleeding time (BT) is used to test the hemostatic effectiveness of infused preparations. The paw of the front leg is warmed by placing it in isotonic saline at 37° C. and a toenail is trimmed to expose only the distal matrix. The bleeding nail is placed in isotonic saline at 37° C. and the time until cessation of bleeding recorded as the primary BT. At 2 to 4 hours, the site is shaved to remove the clot and as little nail matrix as possible. The paw is again placed in saline at 37° C. A discrete stream of extruding blood is visible. With hemophilic dogs in the absence of treatment, bleeding typically continues for 30 min or longer. This time to cessation of bleeding is recorded as a secondary BT. For normal dogs, the primary BT is two to five minutes and the secondary BT is less than five minutes. For hemophilic dogs the primary BT is similar to that of normal dogs while secondary BT is greater than 15 minutes.

Dog #V02 was administered a low dose of FVIIa, 6 μg FVIIa/kg body weight, which was designed to provide only a weak hemostatic effect. After 15 min equilibrium, secondary cuticle bleeding time was measured at 2 min 30 sec, which spontaneously rebled for 5 min 15 sec. Rebleeding challenge (wipe off clot with gauze): 9 min 20 sec bleeding time, which again spontaneously rebled for 15 min, at which time the nail was cauterized to prevent further bleeding. It was difficult to stop bleeding and oozing from the phlebotomy sites in this dog, which continued after FVIIa administration.

The results indicate that this dosage of FVIIa had a very weak hemostatic effect.

The dog was then administered 42 μg tTF/kg body weight. After 15 min equilibration, secondary cuticle bleeding time was measured at 50 sec, which did not spontaneously rebleed. This was dramatically shorter than when the animal had received FVIIa alone. Wiping the clot off with gauze to provoke rebleeding caused rebleeding for only 35 sec, and no subsequent rebleeding was observed. Oozing from two phlebotomy sites in forepaw veins also stopped following infusion of tTF.

The results indicated that tTF in combination with low dose FVIIa has an excellent hemostatic effect.

The same dog was administered 42 μg tTF/kg body weight, without FVIIa, two days later (since the half-lives of both tTF and FVIIa are about 2 hr, this was more than sufficient to ensure clearance of either substance from the plasma). After 15 minutes equilibration, the secondary cuticle bleeding time was greater than 15 minutes and had to be stopped by cauterization.

The results indicated that tTF alone had no measurable hemostatic effect.

The dog was then administered 6 μg FVIIa/kg body weight. After 15 minutes equilibration, secondary cuticle bleeding time was measured at 3 minutes 15 seconds, which did not spontaneously rebleed. Wiping the clot off with gauze caused rebleeding for 3 minutes, and no subsequent rebleeding was observed.

The results again demonstrate that tTF in combination with low dose FVIIa has a very good hemostatic effect.

EXAMPLE 4

Infusion of Factor Xa in combination with phospholipid vesicles (PCPS) to generate Factor VIIa to inhibit bleeding.

Three chimpanzees were infused with a bolus injection of FXa/PCPS as described by Giles, et al., (1988), the teachings of which are incorporated herein by reference. Briefly, factor Xa/PCPS was infused intravenously. The chimpanzee receiving the highest dose received 26 pmoles FXa+40 pmoles PCPS per kg body weight. Plasma samples were drawn at the following times after infusion, giving the indicated plasma FVIIa levels:

|  |  | Plasma FVIIa (ng.mg) |
|---|---|---|
| Pre-infusion |  | 8.0 |
| 2 | min post-infusion | 24.6 |
| 5 | " | 65.4 |
| 10 | " | 125.5 |
| 15 | " | 146.5 |
| 20 | " | 132.0 |
| 20 | " | 101.8 |
| 60 | " | 43.6 |
| 90 | " | 4.4 |

The results indicate that infusion of the tTF in combination with factor Xa/PCPS greatly increased factor VIIa levels.

Modifications and variations of the present invention, a method and compositions for the treatment of excessive bleeding, will be obvious from the foregoing detailed description and are intended to come within the scope of the appended claims.

We claim:

1. A method for treating a patient for excessive bleeding occurring at a site, comprising the step of:

administering an effective amount of a truncated tissue factor protein having an amino acid sequence differing from that of native tissue factor in that sufficient transmembrane amino acids which function to bind native tissue factor to phospholipid membranes are lacking from said truncated tissue factor protein so that said truncated tissue factor protein does not bind to phospholipid membranes, and an effective amount of an activator of endogenous Factor VII to said patient to effect clotting of said patient's blood at said site and subsequent reduction of said excessive bleeding.

2. A method for treating a patient for excessive bleeding occurring at a site, comprising the step of:

administering an effective amount of a truncated tissue factor protein having the amino acid sequence set forth in SEQ ID NO:2 from position 1 to 219 and an effective amount of an activator of endogenous Factor VII to said patient to effect clotting of said patient's blood at said site and subsequent reduction of said excessive bleeding.

3. A method for treating a patient to control bleeding, comprising administering a truncated tissue factor having the amino acid sequence set forth in SEQ ID NO:2 from position 1 to 219 and an activator of endogenous Factor VII to said patient, said truncated tissue factor in a sufficient amount to produce a level of from about 100 nanograms to about 50 micrograms of said truncated tissue factor per milliliter of plasma and said activator of endogenous Factor VII in a sufficient amount to produce a level of from about 20 nanograms to about 700 nanograms Factor VIIa per milliliter of plasma.

4. A method for treating a patient to control bleeding according to claim 3 wherein said truncated tissue factor and said activator of endogenous Factor VII are administered simultaneously to said patient.

5. A method for treating a patient to control bleeding according to claim 3 wherein said truncated tissue factor and said activator of endogenous Factor VII are administered sequentially to said patient.

6. A method for treating a patient to control bleeding according to claim 3 wherein said truncated tissue factor and said activator of endogenous Factor VII are administered systemically to said patient.

7. A method for treating a patient to control bleeding according to claim 6 wherein a sufficient amount of said truncated tissue factor is administered to produce a level of from about 1 microgram to about 10 micrograms truncated tissue factor per milliliter of plasma and wherein a sufficient amount of said activator of endogenous Factor VII is administered to produce a level of between about 40 nanograms and 700 nanograms Factor VIIa per milliliter of plasma.

8. A method for treating a patient to control bleeding according to claim 3 wherein said truncated tissue factor and said activator of endogenous Factor VII are administered topically to a wound site.

9. A method for treating a patient to control bleeding according to claim 8 wherein a sufficient amount of said truncated tissue factor is administered to produce a local concentration in said wound site of from about 10 to about 50 micrograms truncated tissue factor per milliliter of plasma and a sufficient amount of said activator of endogenous Factor VII is administered to produce a local concentration in said wound site of from about 40 nanograms to about 700 nanograms Factor VIIa per milliliter of plasma.

10. A method for treating a patient to control bleeding according to claim 3, wherein said truncated tissue factor and said activator of endogenous Factor VII are administered to control surgical bleeding from the microvasculature.

11. A method for treating a patient to control bleeding according to claim 3, wherein said truncated tissue factor and said activator of endogenous Factor VII are administered to control postoperative bleeding.

12. A method for treating a patient to control bleeding according to claim 3, wherein said truncated tissue factor and said activator of endogenous Factor VII are administered to control bleeding secondary to thrombocytopenia.

13. A method for treating a patient to control bleeding according to claim 3, wherein said truncated tissue factor and said activator of endogenous Factor VII are administered to control bleeding of patients with platelet dysfunction.

14. The method of claim 3, wherein said activator of endogenous Factor VII is selected from the group consisting of Factor Xa in combination with phospholipid, Factor IXa in combination with phospholipid, thrombin, Factor XIIa, and an FVII activator from the venom of *Oxyuranus scutellatus* in combination with phospholipid.

15. The method of claim 3, wherein said activator of Factor VII comprises Factor Xa and phospholipid.

16. The method of claim 15, wherein from about 12 to about 26 pmoles Factor Xa and from about 19 to about 40 pmoles phospholipid per kg body weight of said patient are administered as said activator of Factor VII.

17. A pharmaceutical composition for treating excessive bleeding comprising a truncated tissue factor protein having an amino acid sequence which differs from that of native tissue factor in that sufficient transmembrane amino acids which function to bind native tissue factor to phospholipid membranes are lacking from said truncated tissue factor protein so that said truncated tissue factor protein does not bind to phospholipid membranes, and an activator of endogenous Factor VII.

18. A pharmaceutical composition for systemic administration to a patient to control bleeding, comprising a combination of a truncated tissue factor having the amino acid sequence of SEQ ID NO:2 from position 1 to 219 and an activator of endogenous Factor VII, said truncated tissue factor and said activator of endogenous Factor VII in sufficient quantity to effect clotting of said patient's blood at a desired site.

19. A pharmaceutical composition for topical administration to a patient comprising a pharmaceutically acceptable carrier for topical administration, about 100 nanograms to about 50 micrograms of a truncated tissue factor having the amino acid sequence of SEQ ID NO:2 from position 1 to 219 per milliliter of said carrier and from about 1 to about 10 micrograms of an activator of endogenous Factor VII per milliliter of said carrier.

* * * * *